United States Patent
Shau et al.

(10) Patent No.: US 10,123,701 B2
(45) Date of Patent: Nov. 13, 2018

(54) INTRAOCULAR PRESSURE DETECTING DEVICE AND DETECTING METHOD THEREOF

(71) Applicant: Industrial Technology Research Institute, Hsinchu (TW)

(72) Inventors: Yio-Wha Shau, Taipei (TW); De-Yi Chiou, New Taipei (TW); Wan-Ting Tien, Chiayi (TW); Tian-Yuan Chen, Hsinchu (TW); Chun-Chuan Lin, Hsinchu (TW); Shih-Bin Luo, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 330 days.

(21) Appl. No.: 14/979,596

(22) Filed: Dec. 28, 2015

(65) Prior Publication Data

US 2017/0181626 A1  Jun. 29, 2017

(30) Foreign Application Priority Data

Dec. 23, 2015 (TW) .............................. 104143302 A

(51) Int. Cl.
*A61B 3/16* (2006.01)
*A61B 3/00* (2006.01)
*A61B 3/14* (2006.01)

(52) U.S. Cl.
CPC ............ *A61B 3/165* (2013.01); *A61B 3/0025* (2013.01); *A61B 3/14* (2013.01)

(58) Field of Classification Search
CPC .......... A61B 3/165; A61B 3/14; A61B 3/0025
See application file for complete search history.

(56) References Cited

U.S. PATENT DOCUMENTS

| 3,585,849 A | 6/1971 | Grolman |
| 4,724,843 A | 2/1988 | Fisher |
| (Continued) | | |

FOREIGN PATENT DOCUMENTS

| CN | 1494864 | 5/2004 |
| CN | 1498594 | 5/2004 |
| (Continued) | | |

OTHER PUBLICATIONS

Kim et al., "Intraocular pressure measurement devices using the micro reflected air pressure sensor for the pre-diagnosis of the glaucoma," 2010 10th IEEE Conference on Nanotechnology (IEEE-NANO), Aug. 2010, pp. 907-910.

(Continued)

*Primary Examiner* — Sean Dougherty
(74) *Attorney, Agent, or Firm* — JCIPRNET

(57) ABSTRACT

An intraocular pressure detecting device includes a pressure generation unit, a light source, an image sensing unit and a processing unit. The pressure generation unit applies pressure to a target surface of an eyeball along a first operation axis direction, such that a deformation is generated on the target surface. The light source emits light that irradiates the target surface along a second operation axis direction, so as to generate a speckle pattern on the target surface. The image sensing unit observes and records an image variation of the speckle pattern along a third operation axis direction. The processing unit is signally connected with the image sensing unit to receive an image of the speckle pattern. The processing unit identifies and analyzes a feature size of the image of the speckle pattern for obtaining an intraocular pressure value of the eyeball. An intraocular pressure detecting method is also described.

17 Claims, 11 Drawing Sheets

(56) References Cited

U.S. PATENT DOCUMENTS

| | | | | |
|---|---|---|---|---|
| 4,995,716 | A | * | 2/1991 | Warnicki ............... A61B 3/107 351/212 |
| 5,159,361 | A | * | 10/1992 | Cambier ............... A61B 3/107 351/212 |
| 5,506,632 | A | | 4/1996 | Kohayakawa |
| 6,419,631 | B1 | * | 7/2002 | Luce ...................... A61B 3/165 600/401 |
| 6,875,175 | B2 | * | 4/2005 | Luce ...................... A61B 3/165 600/398 |
| 7,231,243 | B2 | * | 6/2007 | Tearney ............. A61B 1/00082 600/407 |
| 7,418,169 | B2 | * | 8/2008 | Tearney ............. A61B 1/00082 385/11 |
| 7,553,282 | B2 | | 6/2009 | Masaki |
| 7,567,349 | B2 | * | 7/2009 | Tearney ............... A61B 5/0059 356/479 |
| 8,097,864 | B2 | * | 1/2012 | Tearney ............. G01N 21/6458 250/459.1 |
| 8,551,014 | B2 | | 10/2013 | Koest et al. |
| 8,801,668 | B2 | | 8/2014 | Ali et al. |
| 8,900,143 | B2 | | 12/2014 | Yen et al. |
| 2006/0241367 | A1 | | 10/2006 | Koest |
| 2008/0259276 | A1 | * | 10/2008 | Roberts ................. A61B 3/165 351/212 |
| 2009/0030299 | A1 | | 1/2009 | Naito et al. |
| 2009/0177098 | A1 | * | 7/2009 | Yakubo ................... A61B 3/12 600/504 |
| 2012/0253165 | A1 | | 10/2012 | Yen et al. |
| 2012/0265047 | A1 | | 10/2012 | Yen et al. |
| 2012/0330140 | A1 | * | 12/2012 | Yonezawa ........... A61B 3/1225 600/425 |
| 2013/0144137 | A1 | * | 6/2013 | Zalevsky ........... A61B 5/14532 600/314 |
| 2013/0150774 | A1 | * | 6/2013 | Field ................... A61M 1/0031 604/9 |
| 2013/0345619 | A1 | * | 12/2013 | Auld ....................... A61F 9/007 604/24 |
| 2014/0073917 | A1 | * | 3/2014 | Huang ................. A61B 5/0066 600/427 |
| 2015/0148648 | A1 | * | 5/2015 | Pugh ..................... A61F 9/0017 600/398 |
| 2017/0238799 | A1 | * | 8/2017 | Bian .................... A61B 3/0025 |

FOREIGN PATENT DOCUMENTS

| | | |
|---|---|---|
| CN | 101299957 | 11/2008 |
| CN | 101352333 | 1/2009 |
| CN | 102309312 | 1/2012 |
| CN | 102309313 | 1/2012 |
| CN | 102727179 | 10/2012 |
| CN | 103169447 | 6/2013 |
| TW | 201240642 | 10/2012 |
| TW | 201422203 | 6/2014 |
| TW | 201501688 | 1/2015 |
| TW | I474802 | 3/2015 |
| TW | I494638 | 8/2015 |

OTHER PUBLICATIONS

Han et al., "Active non-contact tonometer for glaucoma detection," Proceedings of SPIE, Oct. 2002, pp. 143-150.

Han et al., "The reflectivity of human cornea and its influence on the selection of a suitable light source for a low cost tonometer," Proceedings of SPIE, Oct. 2002, pp. 373-377.

Kaneko et al., "Dynamic Sensing of Human Eye," Proceedings of the 2005 IEEE International Conference on Robotics and Automation, Apr. 2005, pp. 2871-2876.

Robert Koprowski, "Automatic method of analysis and measurement of additional parameters of corneal deformation in the Corvis tonometer," BioMedical Engineering OnLine, Nov. 2014, pp. 1-15.

Koprowski et al., "Scheimpflug camera in the quantitative assessment of reproducibility of high-speed corneal deformation during intraocular pressure measurement," J. Biophotonics, Jan. 2015, pp. 968-978.

Parul Singh, "Tonometry: an overview," IOSR Journal of Dental and Medical Sciences, Jan. 2014, pp. 67-70.

Liang et al., "Self-tonometry in Glaucoma Management—Past, Present and Future," Survey of Ophthalmology, Jul. 2009, pp. 450-462.

Kling et al., "Corneal Viscoelastic Properties from Finite-Element Analysis of In Vivo Air-Puff Deformation," Plos ONE, Aug. 2014, pp. 1-12.

Bhatt et la., "On Imaging based Non-contact Tonometer for Intraocular Pressure Measurement," 2013 IEEE Point-of-Care Healthcare Technologies, Jan. 2013, pp. 97-100.

"Office Action of Taiwan Counterpart Application", dated May 24, 2016, p. 1-p. 4.

"Office Action of China Counterpart Application," dated Jan. 30, 2018, p. 1-p. 7.

\* cited by examiner

| Date | Size | mmHg | ○ |
|---|---|---|---|
| 2015/10/29 01:30:34 | 10.54mm | 16.42 | ✓ |
| 2015/10/29 01:19:11 | 6.21mm | 36.5 | ✗ |

FIG. 8E

INTRAOCULAR PRESSURE DETECTING DEVICE AND DETECTING METHOD THEREOF

CROSS-REFERENCE TO RELATED APPLICATION

This application claims the priority benefit of Taiwan application serial no. 104143302, filed on Dec. 23, 2015. The entirety of the above-mentioned patent application is hereby incorporated by reference herein and made a part of this specification.

TECHNICAL FIELD

The technical field relates to an intraocular pressure detecting device and a detecting method thereof.

BACKGROUND

To maintain elasticity and visual functions of an eyeball, it is necessary to maintain intraocular pressure (IOP) within a certain range. The level of intraocular pressure is related to production and drainage of aqueous humor inside the eyeball. The aqueous humor is produced in the posterior chamber by ciliary processes of the ciliary body, flows through the pupil into the anterior chamber, and then flows from the trabecular meshwork in the corner of the anterior chamber into Schlemm's canal, or flows through uveal tissue gaps and is then recycled into blood via veins. The aqueous humor provides oxygen and nutrients to anterior intraocular tissues and remove metabolic wastes therefrom. A balance between production and drainage of the aqueous humor determines the level of intraocular pressure. If too much aqueous humor is produced or the drainage path is blocked, the intraocular pressure rises. Excessively high intraocular pressure may compress and damage nerves to cause visual field defects and visual acuity reduction, thus resulting in so-called glaucoma.

According to estimates made by the World Health Organization (WHO) and the International Agency for the Prevention of Blindness (IAPB), by 2020, eighty million people worldwide will have glaucoma and more than ten million of them will be bilaterally blind because of the disease. People having excessively high intraocular pressure are in a high-risk group for glaucoma. Clinically, normal intraocular pressure ranges from about 10 to 21 mmHg. Measurement of intraocular pressure is an important factor in controlling development of glaucoma. However, diurnal and nocturnal fluctuation in the intraocular pressure vary from person to person. The intraocular pressure of a normal person fluctuates within 2 to 6 mmHg. A patient with glaucoma has larger intraocular pressure fluctuation, sometimes of more than 10 mmHg. The intraocular pressure measured at the patient's follow-up visit to the doctor is merely an intraocular pressure value at a specific time during a day and does not reflect the diurnal and nocturnal fluctuation in the intraocular pressure. The doctor cannot determine whether the patient's intraocular pressure is under control 24 hours a day based only on this value, and hence cannot determine, in real time, timing of administration, frequency of administration, prescriptions or dosages. Early symptoms of glaucoma are mainly caused by death of optic nerves due to excessively high intraocular pressure over a long period. Among current methods of treating glaucoma, the only one considered reliably effective and capable of effective monitoring is to lower the intraocular pressure. Therefore, an instrument capable of real-time and long-term detection or monitoring of intraocular pressure will contribute to clinical monitoring and treatment of early glaucoma.

However, in terms of current general clinical screening methods, follow-up visits are scheduled about every three months or every half year, and the intraocular pressure measured at each visit is nothing more than an intraocular pressure value at a specific time during that day and cannot truly reflect fluctuation in the intraocular pressure over a long period. Only by long-term and constant tracking of intraocular pressure values, the patient's complete intraocular pressure record can be available to the doctor, who is thus able to actually see fluctuation conditions of the patient's intraocular pressure so as to set target IOP/baseline and safety thresholds particularly for the patient. Therefore, a method is needed for allowing the patient to perform self-detection and self-management of intraocular pressure at home and for enabling long-term and constant tracking of the intraocular pressure.

In addition, among existing medical tonometers, air-puff type non-contact tonometry (NCT) are most extensively used. However, conventional NCT include laser optical alignment and force sensing systems that have complex architecture and large size and are also costly, which makes them hardly acceptable as tonometers for self-detection at home. In addition, applanation tonometers provide a portable and accurate intraocular pressure measurement means. However, during measurement, the applanation tonometers require direct contact with the patient's cornea, and local anesthesia on the patient's eye is necessary. Moreover, the applanation tonometers cannot be operated by the patient themselves. Hence, these devices are not very convenient in use. Recently, implantable intraocular pressure sensors have been launched one after another. While satisfying the need for continuous intraocular pressure monitoring, these devices must be implanted in the eye by surgery and are highly invasive, thus reducing patient acceptance.

Based on the above reasons, it is an important subject in ophthalmology to develop a tonometer that enables self-detection and self-management at home, that is easy and safe to use, that is highly precise, and that has warning and reminder functions in order to solve the aforementioned problems.

SUMMARY

An intraocular pressure detecting device according to an exemplary embodiment of the disclosure includes a pressure generation unit, a light source, an image sensing unit and a processing unit. The pressure generation unit applies pressure to a target surface of an eyeball along a first operation axis direction, such that a deformation is generated on the target surface. The light source emits light that irradiates the target surface along a second operation axis direction, so as to generate a speckle pattern on the target surface. The image sensing unit captures and records an image variation of the speckle pattern along a third operation axis direction. The processing unit is signally connected with the image sensing unit to receive images of the speckle patterns. The processing unit identifies and analyzes a feature size of an image of the speckle pattern, so as to obtain an intraocular pressure level and its value of the eyeball.

An intraocular pressure detecting method according to an exemplary embodiment of the disclosure includes the following steps. Pressure is applied by a pressure generation unit to a target surface of an eyeball along a first operation axis direction, such that a deformation is generated on the target surface. Light is emitted by a light source and irradiates the target surface along a second operation axis direction, and a speckle pattern is generated on the target surface. An image variation of the speckle pattern is captured and recorded by an image sensing unit along a third operation axis direction. By a processing unit, an image of the speckle pattern is received, and a feature size of the image of the speckle pattern is identified and analyzed, such that an intraocular pressure level and its value of the eyeball is obtained.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

FIGS. 8A to 8E are schematic diagrams of software operation interfaces of a processing unit of an intraocular pressure detecting device according to an exemplary embodiment of the disclosure.

DETAILED DESCRIPTION OF DISCLOSED EMBODIMENTS

Figure 1:
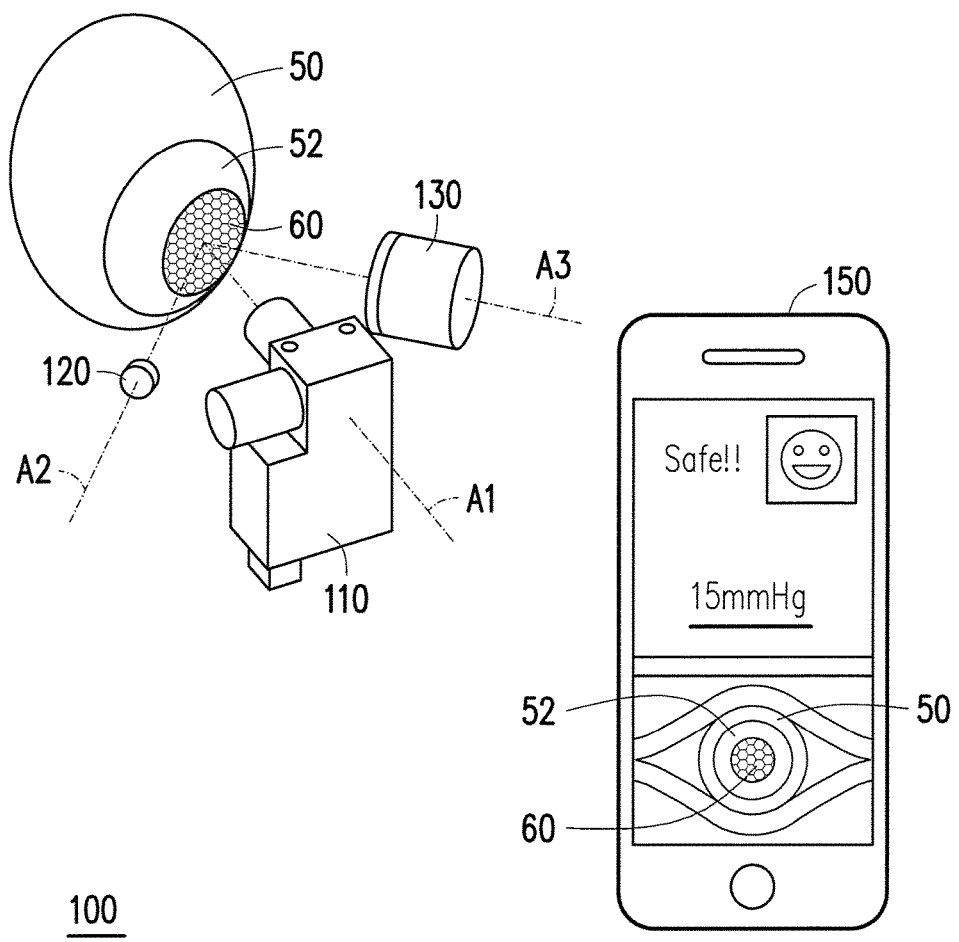
FIG. 1 is a schematic diagram of an intraocular pressure detecting device according to an exemplary embodiment of the disclosure.

FIG. 1 is a schematic diagram of an intraocular pressure detecting device according to an exemplary embodiment of the disclosure. Referring to FIG. 1, in the present exemplary embodiment, an intraocular pressure detecting device 100 includes a pressure generation unit 110, a light source 120, an image sensing unit 130 and a processing unit 150. The pressure generation unit 110 applies pressure to a target surface 52 of an eyeball 50 along a first operation axis direction Al, such that a deformation is generated on the target surface 52. The light source 120 emits light that irradiates the target surface 52 of the eyeball 50 along a second operation axis direction A2, so that the light is scattered to generate a speckle pattern 60 on the target surface 52, wherein the speckle pattern 60 is in the form of a point, a line, a hollow circle or a surface of arbitrary shape. In the present exemplary embodiment, the first operation axis direction A1 and a normal line of the target surface 52 form an angle of 0 to 90 degrees therebetween. The image sensing unit 130 captures and records, along a third operation axis direction A3, an image variation of the speckle pattern 60, particularly a feature size such as diameter, perimeter or area of the speckle pattern 60. The processing unit 150 is signally connected with the image sensing unit 130, and obtains an intraocular pressure value of the target surface 52 according to the feature size of the speckle pattern 60 recorded by the image sensing unit 130.

In addition, as shown in FIG. 1, the processing unit 150 displays a measurement result from the image sensing unit 130, and shows the intraocular pressure value and status of the eyeball 50, so as to provide relevant notification and information to a patient in a timely manner. Moreover, the processing unit 150 transmits the patient's intraocular pressure information to a server of a remote medical facility through, e.g., wireless transmission, such that the patient's intraocular pressure can be effectively monitored.

In the present exemplary embodiment, an angle between the first operation axis direction A1 and the second operation axis direction A2 falls between 0 and 90 degrees. An angle between the first operation axis direction A1 and the third operation axis direction A3 falls between 0 and 90 degrees. An angle between the second operation axis direction A2 and the third operation axis direction A3 falls between 0 and 180 degrees. Alternatively, the first operation axis direction A1, the second operation axis direction A2 and the third operation axis direction A3 may be coplanar or coaxial. In another exemplary embodiment not illustrated, the first operation axis direction A1, the second operation axis direction A2 and the third operation axis direction A3 may not be coaxial, and may not be coplanar with one another. The angles between and relative positions of the first operation axis direction A1, the second operation axis direction A2 and the third operation axis direction A3 in the present exemplary embodiment can be suitably adjusted according to actual needs.

Figure 2:
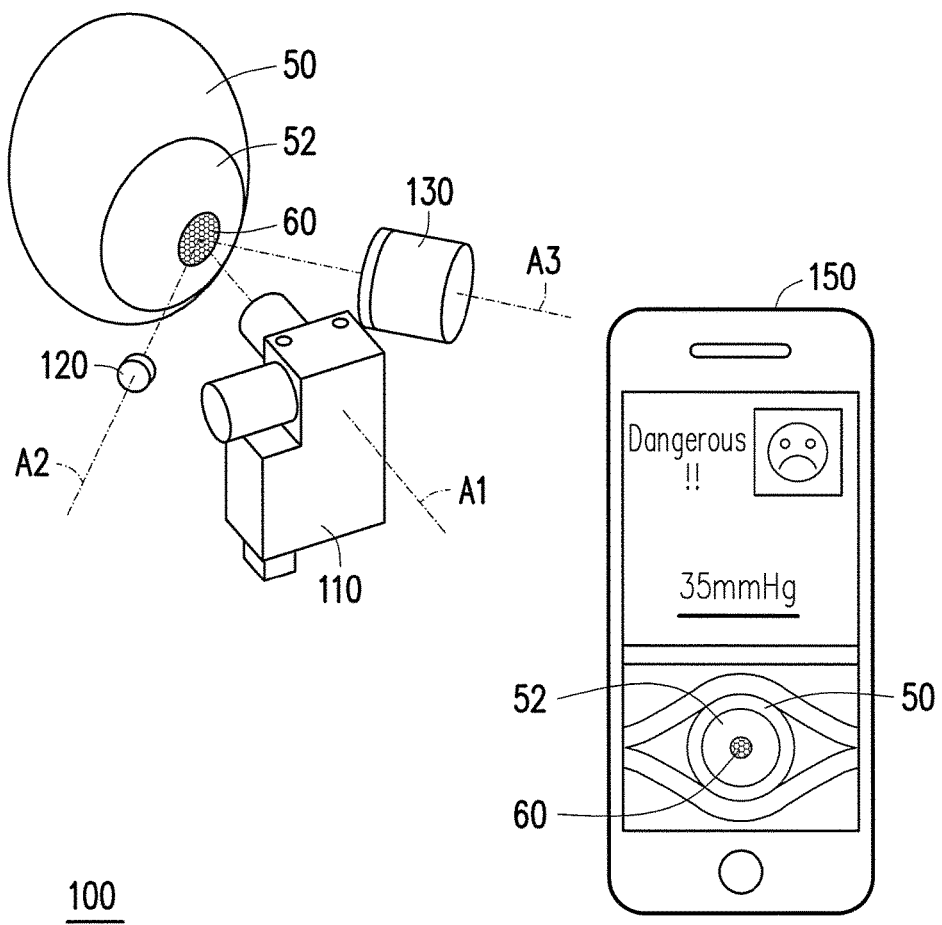
FIG. 2 is a schematic diagram of the intraocular pressure detecting device in FIG. 1 according to another exemplary embodiment.

FIG. 2 is a schematic diagram of the intraocular pressure detecting device in FIG. 1 according to another exemplary embodiment. Referring to FIGS. 1 and 2, when the light source 120 is incident on the target surface 52 on the cornea at a specific incident angle, the speckle pattern 60 is generated on the target surface 52. As shown in FIG. 1, when the intraocular pressure value is lower, the cornea of the eyeball 50 has lower resistance to external force, and a deformation amount of the cornea of the eyeball 50 is larger in the first operation axis direction A1, i.e., the direction in which the pressure generation unit 110 applies pressure, so that the speckle pattern 60 on the target surface 52 also becomes larger.

In the present exemplary embodiment, the pressure generation unit 110 applies pressure to the eyeball 50 by, e.g., applying a non-contact force produced by a physical means such as air, gases, sound waves and electromagnetic waves (air or gases in this example) to the target surface 52, such that a deformation is generated on the target surface 52 of the eyeball 50. The target surface 52 is located on the cornea of the eyeball 50. By use of a contrast characteristic (1.376:1) in refractive index between the cornea and the air, a non-invasive method is performed by, e.g., irradiation with the light source 120 at a specific incident angle to generate the speckle pattern 60, also called a catchlight. Next, image information of variation in the speckle pattern on the cornea is further captured. When the intraocular pressure is low, the cornea has lower resistance to external force, and thus the amount of deformation of the cornea generated in the axis direction is larger, and the speckle pattern 60 has a larger diaphragm contour. In contrast, when the intraocular pressure is high, the cornea has higher resistance to external force, and thus the amount of deformation of the cornea in the axis direction is smaller, and the speckle pattern 60 has a smaller diaphragm contour. In other words, the disclosure utilizes the diaphragm contour (transverse variation) of the speckle pattern 60 for reflecting the actual corneal deformation (axial variation). Generally, since corneal deformation in the axis direction is very slight in amount, measurement thereof is quite difficult. In contrast, variation in size of the diaphragm contour in the eye is relatively noticeable. Therefore, by measuring the transverse variation in diaphragm contour on the cornea for reflecting the corneal deformation in the axis direction, the problem that the intraocular pressure value of the eyeball is not easy to measure is solved.

Figure 3A:
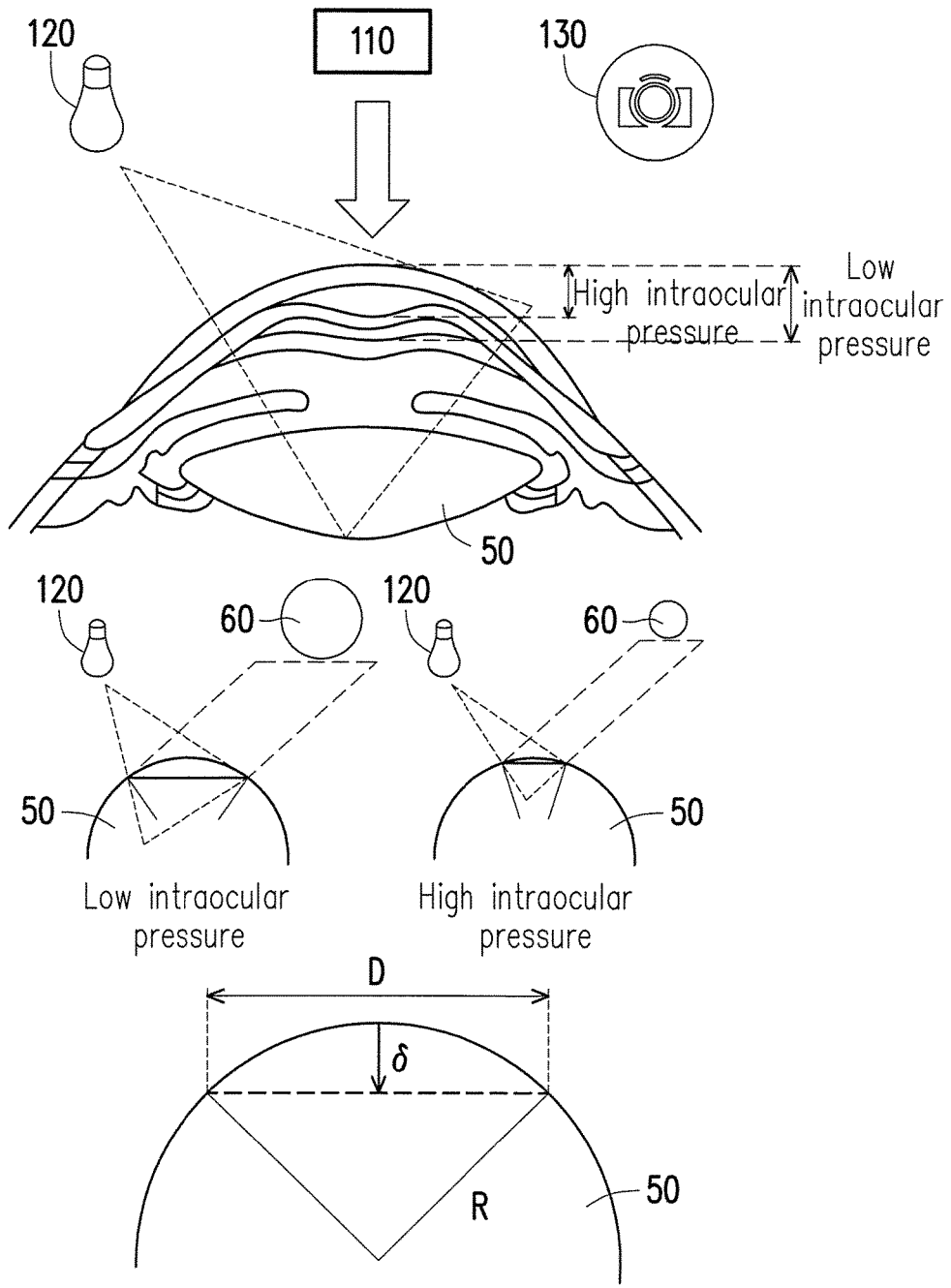
FIGS. 3A and 3B are schematic diagrams of working principles of the intraocular pressure detecting device in FIG. 1.
Figure 3B:
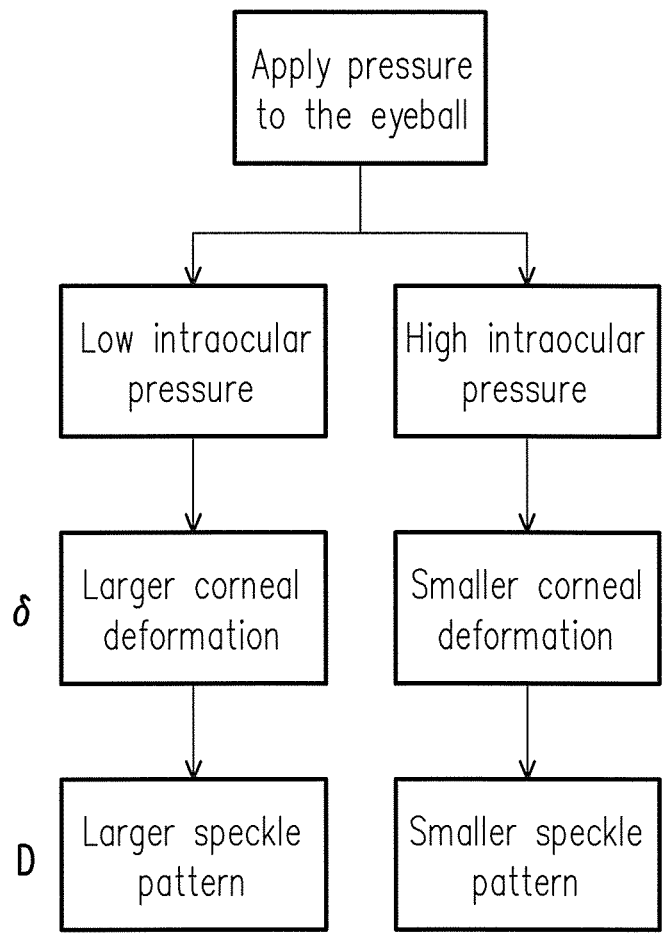

FIGS. 3A and 3B are schematic diagrams of working principles of the intraocular pressure detecting device in FIG. 1. Please refer to FIGS. 3A and 3B. In detail, when pressure is applied to a surface of the eyeball 50 by air puffing and when the intraocular pressure of the eyeball 50 is lower, a larger deformation occurs at the corneal apex of the eyeball 50, so that the cornea has a larger air-puff deformed area. Therefore, when the light source 120 irradiates the cornea of the eyeball 50, the speckle pattern 60 having a larger area is formed on the surface of the cornea. In contrast, when pressure is applied to the surface of the eyeball 50 and when the intraocular pressure of the eyeball 50 is higher, a smaller deformation occurs at the corneal apex of the eyeball 50, so that the cornea has a smaller air-puff deformed area. Therefore, when the light source 120 irradiates the cornea of the eyeball 50, the speckle pattern 60 having a smaller area is formed on the surface of the cornea.

In the present exemplary embodiment, in FIG. 3A, a relation derived function between an axial deformation amount δ of the apex of cornea, a radius R of the cornea and size D of the air-puff flatten area (speckle pattern) caused by air puffing is expressed by the following equation (1):

$$D=2*(2*R*\delta-\delta^2)^{1/2} \quad (1)$$

This function indicates that the size D of the speckle pattern and the axial deformation amount δ of the cornea have a slightly nonlinear relationship (polynomial of degree 1.5), which indirectly proves the aforementioned background theory of the disclosure. In addition, the above equation explains the relationship between speckle pattern size and corneal deformation in the axis direction, and illustrates that the variation in the speckle pattern size can reflect the variation in the intraocular pressure value.

Figure 4:
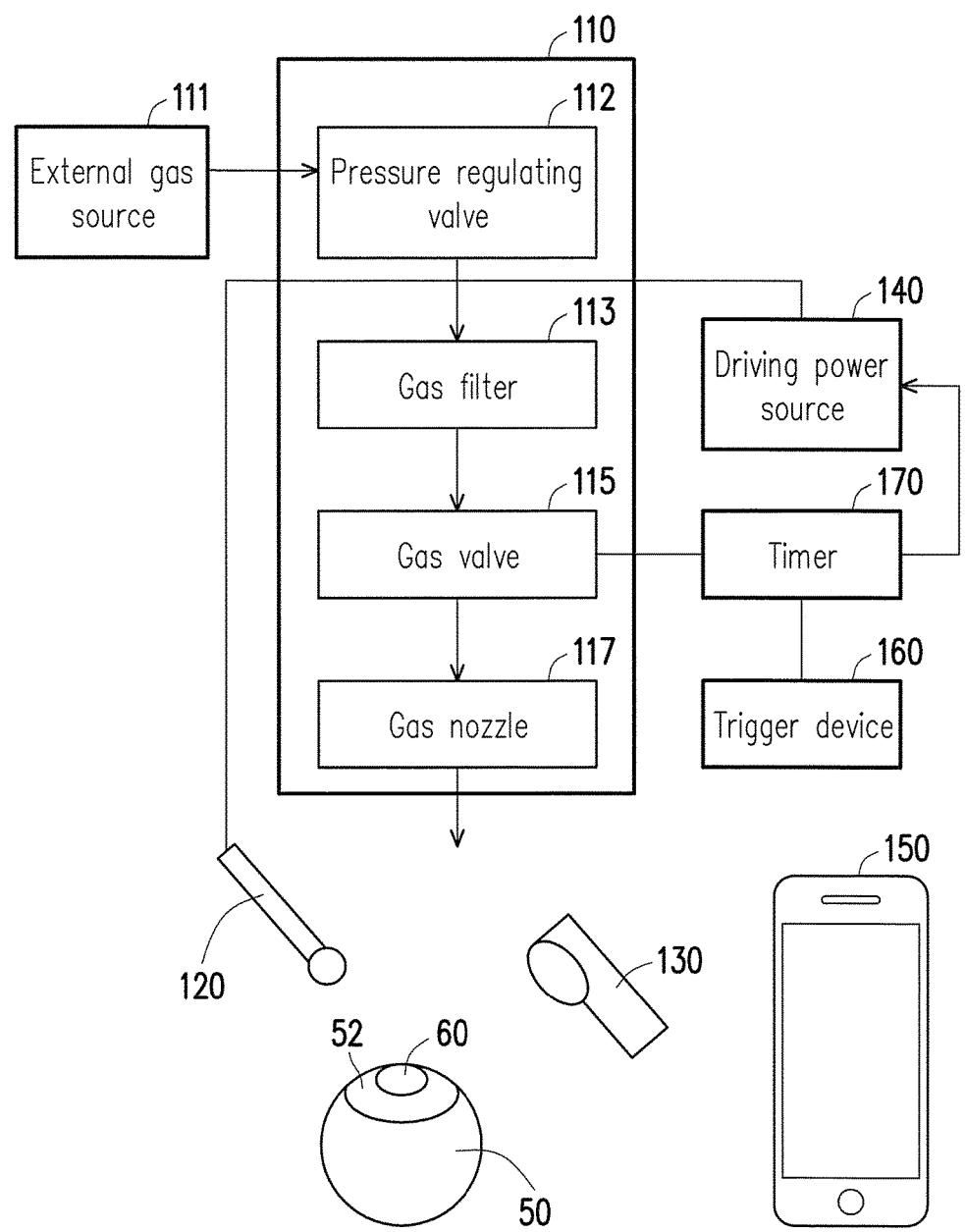
FIG. 4 is an architecture diagram of an intraocular pressure detecting device according to an exemplary embodiment of the disclosure.

FIG. 4 is an architecture diagram of an intraocular pressure detecting device according to an exemplary embodiment of the disclosure. As shown in FIG. 4, in the architecture diagram of the intraocular pressure detecting device 100 in the present exemplary embodiment, the pressure generation unit 110 applies an external loading force to the target surface 52 of the eyeball 50 by, e.g., air-puff jetting. The pressure generation unit 110 includes an external gas source 111, a pressure regulating valve 112, a gas filter 113, a gas valve 115, and a gas nozzle 117. The external gas source 111 is an external pressure source storage device that includes an air pump or a pre-charged pneumatic device. In addition, the pre-charged pneumatic device is a compressed gas cylinder or a manually chargeable pneumatic device. The gas nozzle 117 in the present exemplary embodiment has a diameter ranging from, e.g., 0.5 to 5 mm. The gas jetting from the pressure generation unit 110 includes carbon dioxide, nitrous oxide, nitrogen or oxygen, etc.

The gas nozzle 117 is connected to the gas valve 115, and the gas valve 115 is disposed between the pressure regulating valve 112 and the gas nozzle 117. A timer 170 controls the opening time of the gas valve 115 so as to control the gas flow rate and the operating time. In the present exemplary embodiment, the gas valve 115 is electromagnetically or mechanically driven. In addition, the gas valve 115 is electrically connected to the timer 170, and the timer 170 is electrically connected to a driving power 140 so as to control the opening time and the closing time of the gas valve 115. Moreover, the timer 170 is electrically connected to a trigger device 160, and the trigger device 160 controls on and off of the timer 170 and the driving power 140. In the present exemplary embodiment, the pressure generation unit 110 applies pressure to the target surface 52 in a positive direction by a soft pulse air column in a fixed amount or a small amount. The soft pulse air column has a pulse time of less than 50 ms.

In the present exemplary embodiment, the light source 120 is visible light or invisible light, wherein the visible light is an artificial light source or ambient light. For example, the artificial light source may be a light-emitting diode, an organic light-emitting diode, a tungsten light bulb or a fluorescent tube, etc. The ambient light may be natural light, such as sunlight, or scattered light generated by the aforementioned artificial light source. When the light source 120 is invisible light, the invisible light has a wavelength ranging from 800 to 1064 nm.

In the present exemplary embodiment, the image sensing unit 130 includes a photosensitive device, a lens set, an image storage device and a control circuit, etc. In addition, the photosensitive device includes a one-dimensional or two-dimensional charge-coupled device (CCD) image sensor or complementary metal-oxide-semiconductor (CMOS) image sensor. The lens set of the image sensing unit 130 is disposed between the photosensitive device and the target surface 52. The lens set consists of one or a plurality of lens devices that include a microlens, a polarizer or a filter lens, etc. In the present exemplary embodiment, the image sensing unit 130 is signally connected with the processing unit 150 through a wired or wireless transmission interface. The wired transmission interface is, e.g., a universal serial bus (USB) connector interface, an RS-232 interface, or a high-definition multimedia interface (HDMI), etc.; the wireless transmission interface is, e.g., a Wi-Fi wireless transmission interface or a Bluetooth wireless transmission interface, etc. The image sensing unit 130 transmits a captured and recorded image of the speckle pattern 60 to the processing unit 150 through the aforementioned transmission interface.

The processing unit 150 is a mobile device, a wearable device, a computer device or a remote server device, etc., and includes a data processing unit such as an embedded system or an application software for mobile devices. The exemplary embodiments of the disclosure do not impose any limitations on the form of the processing unit 150. The image sensing unit 130 captures an image of the eyeball 50 to obtain a static image or a dynamic image of the speckle pattern 60. Then, the processing unit 150 reads the static image or dynamic image that has been accessed. Next, the processing unit 150 carries out an image analysis and identification on the speckle pattern 60, so as to obtain a feature size such as the diameter, perimeter or area of the speckle pattern 60.

Figure 5:
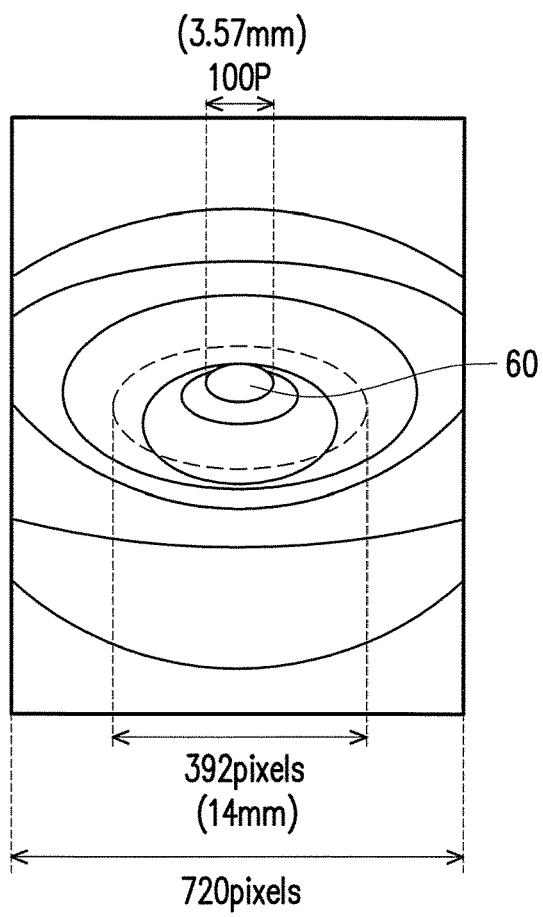
FIG. 5 is a schematic diagram of a method of identifying a speckle pattern size according to an exemplary embodiment of the disclosure.
Figures 8A, 8B:
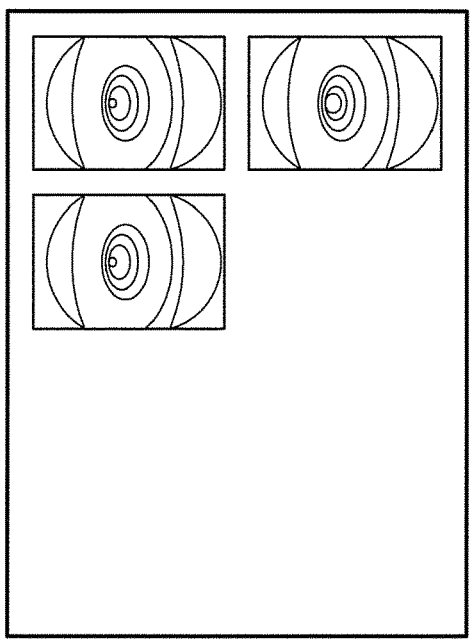

FIG. 5 is a schematic diagram of a method of identifying a speckle pattern size according to an exemplary embodiment of the disclosure. Referring to FIG. 5, in the present exemplary embodiment, the method of identifying the size of the speckle pattern 60 includes quantification of the diameter of the speckle pattern 60 or of the size of white pixels or by other methods. For example, as shown in FIG. 5, when a video of the speckle pattern 60 captured by the image sensing unit 130 is in, e.g., an H.264 coding format, an image captured from the video has a resolution of 1280×720 pixels, which means the entire displayed image has a width corresponding to 720 pixels. Therefore, as the diameter of the corneal limbus boundary of a human eye is generally 14 mm, by comparing this diameter with the width of the entire displayed image, it is obtained that the diameter of the corneal limbus boundary corresponds to 392 pixels. In the present exemplary embodiment, during recording and capturing of the image of the speckle pattern 60, the image sensing unit 130 automatically identifies a scale relationship between the diameter of the corneal limbus boundary and the corresponding pixel number, and automatically transmits the scale relationship to the processing unit 150. Alternatively, a user may manually input the scale relationship to the processing unit 150 through a software operation interface (as shown in FIG. 8A described later). According to conversion of the scale relationship, the width of each of the pixels in FIG. 5 is equal to 0.0357 mm. Thus, when the diameter of the speckle pattern 60 is equivalent to 100 pixels, the diameter of the speckle pattern 60 is calculated to be 3.57 mm.

Accordingly, in the present exemplary embodiment, in measuring the size of the speckle pattern 60, the processing unit 150 can obtain the diameter of the speckle pattern 60 on the cornea by taking the corneal limbus boundary of the eyeball 50 as a reference and by using the relative concept of the scale. In addition to diameter, the feature size of the speckle pattern 60 may also be exemplified by perimeter, area or other features of the speckle pattern 60. In addition, the processing unit 150 includes an application software for carrying out an image data analysis on the speckle pattern 60. In detail, the processing unit 150 converts a dynamic image captured by the image sensing unit 130 into static images at various time points, or directly receives a plurality of static images obtained by the image sensing unit 130 by continuous shooting. Next, the processing unit 150 measures and compares the feature sizes of the speckle pattern 60 in each image and selects an image of the speckle pattern 60 for subsequent identification and analysis. For example, the processing unit 150 selects an image of the speckle pattern 60 having a larger feature size for subsequent identification and analysis. In addition, the processing unit 150 compares the feature size of the selected speckle pattern 60 with the feature size of the speckle pattern 60 corresponding to a normal intraocular pressure value, so as to determine whether the intraocular pressure value of the eyeball 50 falls within the normal range.

In the present exemplary embodiment, the size of the speckle pattern 60 corresponding to each different patient's intraocular pressure value is not absolute but depends on personal factors such as the patient's eyeball structure, the environment and so on. That is, even the actual intraocular pressure values of different patients are the same, the measured sizes of the speckle patterns 60 may be still different. Accordingly, before the intraocular pressure detecting device 100 is utilized in the measurements, the corresponding correction processes for determining the relationship between the actual intraocular pressure values and the sizes of the speckle patterns 60 should be applied. Therefore, after a size value of the speckle pattern of the patient is derived by the intraocular pressure detecting device 100, the patient may undergo the measurement using a medical tonometer instrument, e.g., a Goldmann applanation tonometer (GAT), an air puff tonometer or a non-contact tonometer (NCT), at a medical facility, and thus the relationship between the actual intraocular pressure values and the sizes of the speckle patterns 60 can be determined. The aforementioned process may be executed once or more than once (e.g., twice, or preferably many times), and with increment of the measurement times, a more precise predicting curve can be obtained. Accordingly, when the patient has completed the intraocular pressure value measurement at least once, the processing unit 150 obtains one or more intraocular pressure values and measured values of the corresponding feature sizes of the speckle patterns 60.

Figure 6:
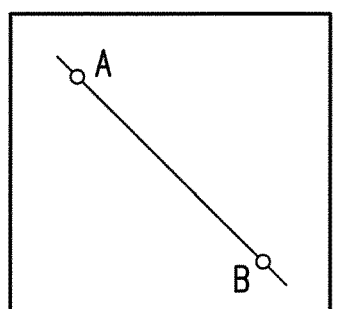
FIG. 6 is a schematic diagram of a relationship between intraocular pressure value and speckle pattern size according to an exemplary embodiment of the disclosure.

FIG. 6 is a schematic diagram of a relationship between intraocular pressure value and speckle pattern size according to an exemplary embodiment of the disclosure. For example, as shown in Table 1, the patient's intraocular pressure measured using the medical tonometer instrument at the medical facility is 34.6 mmHg, the size of the speckle pattern 60 corresponding to the intraocular pressure is obtained as 2.6 mm (as shown by point A in FIG. 6). In addition, after the patient has alleviated the disease by taking medication, the intraocular pressure is lowered to 15.4 mmHg, and the size of the speckle pattern 60 measured by the medical tonometer instrument at this moment is 4.7 mm. Therefore, in the present exemplary embodiment, the doctor performs the measurement using the medical tonometer instrument to obtain two intraocular pressure values and the corresponding sizes of the speckle pattern 60 (i.e., the values on the y-axis corresponding to points A and B in FIG. 6), and according to the at least two intraocular pressure values and the corresponding sizes of the speckle pattern 60, obtains a personalized linear functional relation between the intraocular pressure value and the size of the speckle pattern 60, so as to establish a personalized characteristic function of intraocular pressure with respect to speckle pattern contour, and a corresponding lookup table.

For example, the intraocular pressure detecting device 100 establishes the following characteristic equation (2) of linear functions using the numerical values corresponding to points A and B:

$$y = \left(\frac{y2-y1}{x2-x1}\right)*x + \left(y1 - \left(\frac{y2-y1}{x2-x1}\right)x1\right) \quad (2)$$

In the equation, values of x1 and x2 are respectively the values of the size of the speckle pattern 60 corresponding to points A and B, and are 2.6 and 4.7 as in the present exemplary embodiment. In addition, y1 and y2 are respectively intraocular pressure values corresponding to points A and B, and are, e.g., 34.6 and 15.4 as mentioned above. Moreover, x is the value of the size of the speckle pattern 60 measured by the intraocular pressure detecting device 100. By substituting x into the aforementioned characteristic equation (2), a corresponding intraocular pressure value y is obtained.

In addition, subsequently, when the patient has completed the measurement three times or more using the medical tonometer instrument, the doctor obtains the measured values of the contour size of the speckle pattern 60 corresponding to three or more intraocular pressure values of the patient, and according to the three or more measured values, obtains a nonlinear (curve) functional relation between the size of the speckle pattern 60 and the intraocular pressure value. Meanwhile, after each time the patient has completed the measurement of intraocular pressure using the medical tonometer instrument, the measurement result from the medical tonometer instrument is inputted to the intraocular pressure detecting device 100 for performing correction. In other words, as the number of times of the patient undergoing the measurement at the medical facility increases and the amount of the obtained measurement data increases, a relative relationship or a characteristic equation between the size of the speckle pattern 60 and the intraocular pressure value of each individual patient can be more accurately defined. Thus, afterwards, the corrected intraocular pressure detecting device 100 is capable of more precisely identifying and defining the patient's intraocular pressure value corresponding to the size of the speckle pattern 60. In addition, a curve function between the size of the speckle pattern 60 and the intraocular pressure value obtained after the patient has undergone the measurement many times more closely approximates to the patient's personal measurement curve of intraocular pressure value as the number of times of performing the measurement increases. Therefore, the intraocular pressure value directly calculated from the curve function also more closely approaches that in the lookup table established based on the patient's actual measured values. Moreover, the functional relation expressed by the aforementioned equation (1), i.e., a correspondence between the size of the speckle pattern 60, the axial deformation amount of the cornea and the intraocular pressure value, is indirectly proved.

In the present exemplary embodiment, according to the fluctuation conditions of the patient's intraocular pressure, the doctor sets a threshold and inputs it to the intraocular pressure detecting device 100. Accordingly, when the contour size of the speckle pattern 60 measured by the patient at home using the intraocular pressure detecting device 100 is larger than that corresponding to the threshold, the patient may determine that the intraocular pressure value is within a safe range. However, when the size of the speckle pattern 60 measured by the patient using the intraocular pressure detecting device 100 is smaller than that corresponding to the threshold, the patient may determine that the intraocular pressure value is outside the safe range and they should immediately take medication for alleviation or return to the doctor.

Figure 7:
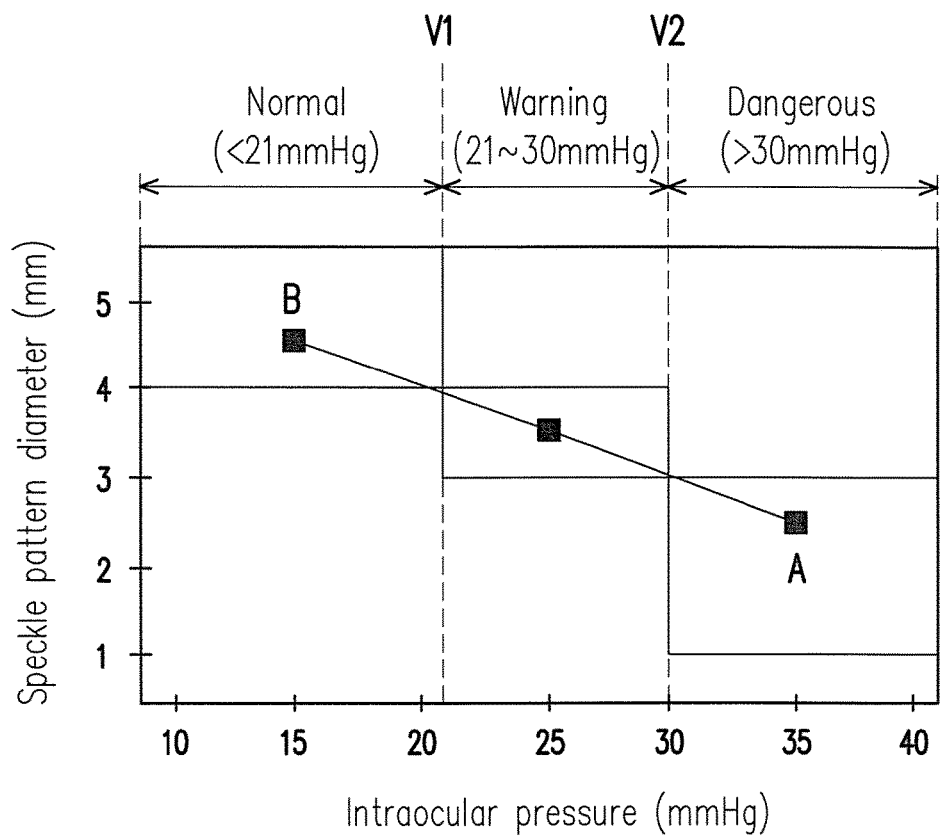
FIG. 7 illustrates a relationship between intraocular pressure value and speckle pattern size according to an exemplary embodiment of the disclosure.

FIG. 7 illustrates a relationship between intraocular pressure value and speckle pattern contour size according to an exemplary embodiment of the disclosure. Referring to Table 1 and FIG. 7, the relationship diagram in FIG. 7 is illustrated according to the measurement results shown in Table 1. In the present exemplary embodiment, the doctor measures the patient's intraocular pressure value once (e.g., at the patient's first visit in which the intraocular pressure value is usually higher and abnormal), and defines a speckle pattern size and a corresponding intraocular pressure correction value for a first point by looking up the standard intraocular pressure values. For example, point A in FIG. 7 represents a speckle pattern size of 2.6 mm, and its corresponding intraocular pressure correction value is 34.6 mmHg. During the period until their next visit to the hospital to measure the intraocular pressure, the patient uses the speckle pattern size represented by point A and the corresponding intraocular pressure correction value as determination references. During this period, if a measured speckle pattern size is larger than 2.6 mm, the intraocular pressure condition is interpreted as safe, and if the speckle pattern size is smaller than 2.6 mm, the intraocular pressure condition is interpreted as dangerous, and the patient should immediately take medication or go to the doctor. Generally, if the patient takes medication in accordance with the doctor's instructions, their intraocular pressure will gradually decrease to normal. Then, at the patient's next (e.g., the second) visit to the hospital to measure the intraocular pressure for the second time, a speckle pattern size of 4.7 mm represented by point B is obtained, and the corresponding intraocular pressure correction value is 15.4 mmHg. At this moment, according to the intraocular pressure values and speckle pattern contour sizes measured at the patient's these two visits (i.e., the visits to the hospital at different times), the doctor establishes a personalized characteristic function of intraocular pressure with respect to speckle pattern contour size, and this function is linear. In addition, according to a relationship diagram illustrated based on the characteristic function, the doctor further sets, for the patient's personal intraocular pressure condition, two or more target IOPs as thresholds (safety IOP baseline), i.e., a first threshold V1 and a second threshold V2 shown in FIG. 7. Moreover, the doctor defines a safe range, a warning range and a dangerous range according to the first threshold V1 and the second threshold V2.

TABLE 1

| | Intraocular pressure value (mmHg) | | |
|---|---|---|---|
| | 15.4 | 25.1 | 34.6 |
| Speckle pattern size (mm) (average value obtained by performing the measurement 10 times) | 4.7 ± 0.12 | 3.6 ± 0.07 | 2.6 + 0.04 |

For example, according to the measurement results shown in Table 1 above, the doctor takes 21 mmHg as the first threshold V1 between the safe range and the warning range, and the corresponding size of the speckle pattern 60 is approximately 4 mm. The doctor then takes 30 mmHg as the second threshold V2 between the warning range and the dangerous range, and the corresponding size of the speckle pattern 60 is approximately 3 mm. Based on this partition, when the feature size (e.g., diameter) of an image contour of the speckle pattern 60 measured by the patient at home using the intraocular pressure detecting device 100 is larger than 4 mm and the corresponding intraocular pressure value is smaller than the first threshold V1 of 21 mmHg, it is interpreted that the patient's intraocular pressure value is within the normal range. When the contour size of the speckle pattern 60 is smaller than 3 mm and the corresponding intraocular pressure value is larger than the second threshold V2 of 30 mmHg, it is interpreted that the patient's intraocular pressure value falls within the dangerous range. When the contour size of the speckle pattern 60 is between 3 mm and 4 mm and the corresponding intraocular pressure value is between the first threshold V1 and the second threshold V2 (i.e., between 21 mmHg and 30 mmHg), it is interpreted that the intraocular pressure value falls within the warning range.

According to the definitions of the thresholds and the partition, the three ranges including the normal range, the warning range and the dangerous range as shown in the relationship diagram in FIG. 7 are set, and a personalized lookup table of intraocular pressure with respect to speckle pattern contour is generated based on the correspondence shown in the relationship diagram and is used for promptly determining whether the patient's intraocular pressure value is outside the safe range. Particularly, when the intraocular pressure value of the eyeball 50 falls within the warning range or the dangerous range, the processing unit 150 issues a warning notification in the form of text, sound, image, light signal or vibration, etc. so as to alert and remind the patient. In the present exemplary embodiment, the three ranges including the safe range, the warning range and the dangerous range of each patient are defined according to the characteristics of the patient's personal characteristic curve of intraocular pressure with respect to speckle pattern contour and the thresholds based on the target IOPs (Safety IOP baseline) given by the doctor.

As shown in the present exemplary embodiment, when the diameter of the speckle pattern 60 is identified as 2.6 mm, by referring to the aforementioned personalized lookup table to obtain that the corresponding intraocular pressure is about 34 mmHg, it is possible to alert the user that their intraocular pressure falls within the warning range and thus medication should be taken or a visit to the doctor should be made as soon as possible.

It is worth mentioning that in the present exemplary embodiment, standard prosthetic human eyes with configurable intraocular pressure values are used. At three different intraocular pressure values including low, medium and high, image information of the speckle pattern is captured, and the contour of the speckle pattern 60 is identified and measured. After a measurement test for the size of speckle pattern 60 corresponding to each different intraocular pressure value has been repeated a plurality of times (e.g., 10 times in this example), the average values are calculated. The average value of the feature size (e.g., diameter) of the speckle pattern 60 obtained by performing the measurement a plurality of times using the medical tonometer instrument is used as a basis for correction of the processing unit 150. In addition, from the relationship between intraocular pressure value and speckle pattern size shown in Table 1, the processing unit 150 infers a variation in the intraocular pressure value caused by a change in the size of the speckle pattern 60. The results in Table 1 show that a negative correlation exists between intraocular pressure and speckle pattern contour size. Moreover, after repeated tests, it is shown that these data are highly reproducible and reliable.

FIGS. 8A to 8E are schematic diagrams of software operation interfaces of a processing unit of an intraocular pressure detecting device according to an exemplary embodiment of the disclosure. The processing unit in the present exemplary embodiment includes an application software. As shown in FIG. 8A, on a software setting interface, the patient enters in dialog boxes on the setting interface the intraocular pressure values of the aforementioned points A and B, i.e., 34.6 mmHg and 15.4 mmHg, and the corresponding contour sizes of the speckle pattern 60, i.e., 2.6 mm and 4.7 mm, so as to establish the aforementioned linear functional relation in the intraocular pressure detecting device 100. In addition, the patient also inputs the first threshold V1 and the second threshold V2 instructed or suggested by the doctor, i.e., 21 mmHg and 30 mmHg, to the setting interface. As mentioned above, the image sensing unit 130 automatically identifies the scale relationship between the diameter of the corneal limbus boundary and the corresponding pixel number, and automatically transmits the same to the processing unit 150. Alternatively, the user may manually input the scale relationship to the software setting interface in FIG. 8A. For example, in FIG. 5A, the diameter of the corneal limbus boundary is 14 mm and the corresponding pixel number is 392. The user may manually input the scale relationship obtained from FIG. 5A to the setting interface in FIG. 8A, so as to use it as a reference for conversion between an image pixel and a corresponding diameter for the speckle pattern 60.

Next, as shown in FIG. 8B, the application software receives a dynamic or static image captured by the image sensing unit 130, wherein when the image received is a dynamic image, the application software converts the dynamic image into static images at various time points. Then, the application software identifies the image size of the speckle pattern 60 according to the static images, and selects, e.g., an image having a larger speckle pattern 60, for subsequent analysis. Next, the application software identifies and analyzes the feature size such as the diameter of the speckle pattern 60, and substitutes this value into the aforementioned characteristic equation, so as to calculate the corresponding intraocular pressure value.

Figure 8C:
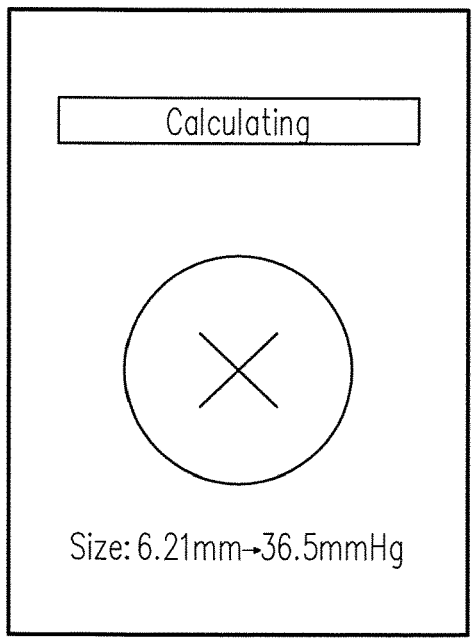
Figure 8D:
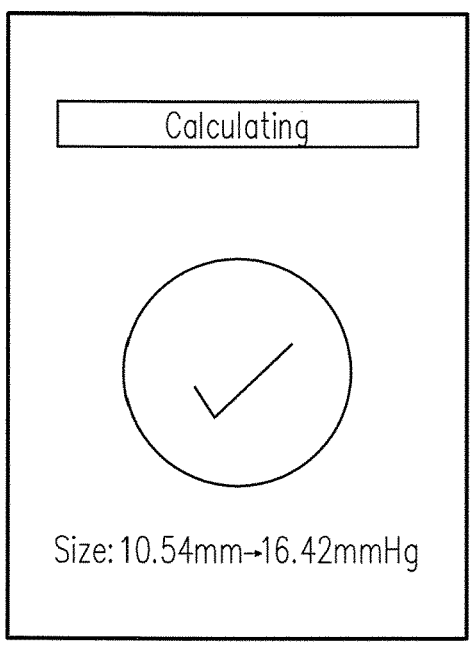

For example, as shown in FIG. 8C, when the measured size of the speckle pattern 60 is 6.21 mm, the intraocular pressure calculated based thereon is 36.5 mmHg. Since the intraocular pressure value of 36.5 mmHg has exceeded the set second threshold V2 (i.e., the threshold of 30 mmHg for the warning range), a display interface of the application software displays a notification such as a danger sign or light signal, etc. As shown in FIG. 8D, when the measured size of the speckle pattern 60 is 10.54 mm, the intraocular pressure calculated based thereon is 16.42 mmHg. Since 16.42 mmHg is smaller than the set first threshold V1 of 21 mmHg, the application software determines that the patient's intraocular pressure falls within the safe range, and issues a notification such as a sign or light signal indicating that the detection result is safe. Finally, as shown in FIG. 8E, the application software of the processing unit 150 records and stores all the measurement results for the patient's reference in daily intraocular pressure management.

Accordingly, when the patient has obtained the feature size (e.g., diameter) of the speckle pattern 60 by measurement at home using the intraocular pressure detecting device 100, the intraocular pressure detecting device 100 automatically substitutes the obtained numerical value of the contour of the speckle pattern 60 into the aforementioned characteristic equation so as to calculate the corresponding intraocular pressure value, or directly obtains the corresponding intraocular pressure value from the aforementioned lookup table.

Figure 9:
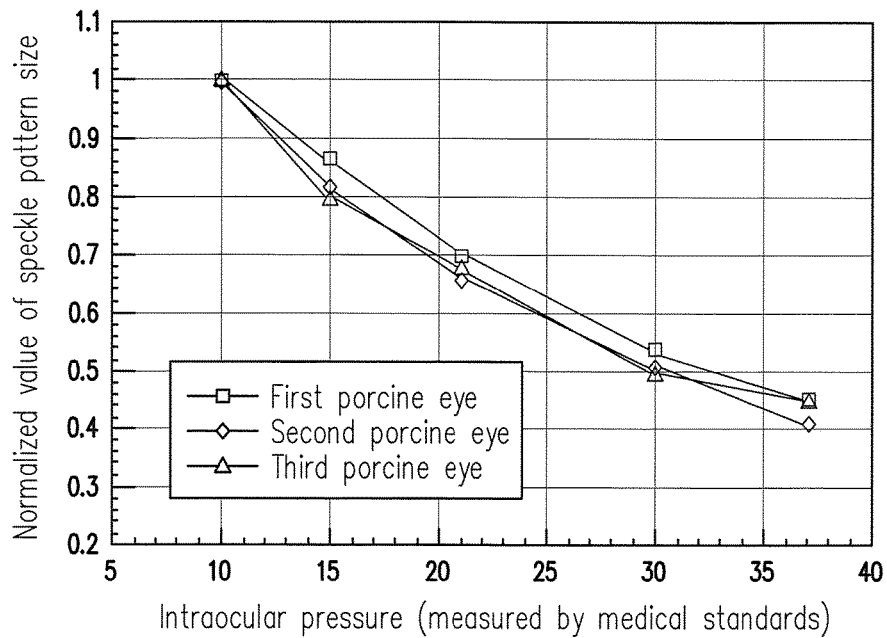
FIG. 9 is a schematic diagram of a relationship between intraocular pressure value and speckle pattern size according to another exemplary embodiment of the disclosure.

FIG. 9 shows a relationship between intraocular pressure value and speckle pattern contour size according to another exemplary embodiment of the disclosure. The present exemplary embodiment replaces the bionic prosthetic human eye used as the measurement target in the exemplary embodiment in FIG. 2 with an in-vitro porcine eye. In Table 2, with three different intraocular pressure values including low, medium and high (10 mmHg, 21 mmHg and 30 mmHg), actual speckle pattern contour size of three different porcine eyes (a first porcine eye, a second porcine eye and a third porcine eye) are measured and corrected by using the medical tonometer instrument. Moreover, the speckle pattern contour is identified and measured using the disclosure, and a diaphragm value of 10 mmHg is used as a relative reference value. Thereby, normalized values of the speckle pattern contour size of the first porcine eye, the second porcine eye and the third porcine eye corresponding to the above intraocular pressure values are obtained and used for observation of relative variation in various curves. For example, when the intraocular pressure of the first porcine eye is 21 mmHg, the speckle pattern size is 0.7 time that at the intraocular pressure of 10 mmHg; when the intraocular pressure of the first porcine eye is 30 mmHg, the speckle pattern size is 0.54 time that at the intraocular pressure of 10 mmHg. Moreover, both the second porcine eye and the third porcine eye have a specific ratio relationship between intraocular pressure and corresponding speckle pattern size, which is similar to the concept of human intraocular pressure that each person has their personal characteristic function between speckle pattern and intraocular pressure. The relationship diagram in FIG. 9 is illustrated according to the intraocular pressure values and the normalized values of the speckle pattern size in Table 2.

TABLE 2

| Intraocular pressure value (mmHg) | | 10 | 21 | 30 |
|---|---|---|---|---|
| Normalized value of speckle pattern size (mm) | First porcine eye | 1 | 0.7 | 0.54 |
| | Second porcine eye | 1 | 0.66 | 0.51 |
| | Third porcine eye | 1 | 0.68 | 0.5 |

According to the measurement results of the first porcine eye, the second porcine eye and the third porcine eye in Table 2, the curves in the relationship diagram in FIG. 9 are illustrated. It is worth mentioning that in the relationship diagram, the curves of the first porcine eye, the second porcine eye and the third porcine eye have similar trends. They all indicate a negative correlation and they all are multilinear. Also, the measurement results of the different porcine eyes at the different intraocular pressure values are very close to each other. From the above measurement results, it can be assumed that the porcine eyes also have an intraocular pressure characteristic curve that tends to be linear (which is at least a quadratic curve) and is predictable. Therefore, a characteristic curve of the intraocular pressure value of a certain porcine can be obtained by performing correction using three or more sets of standard intraocular pressures and corresponding speckle pattern sizes.

Figure 10:
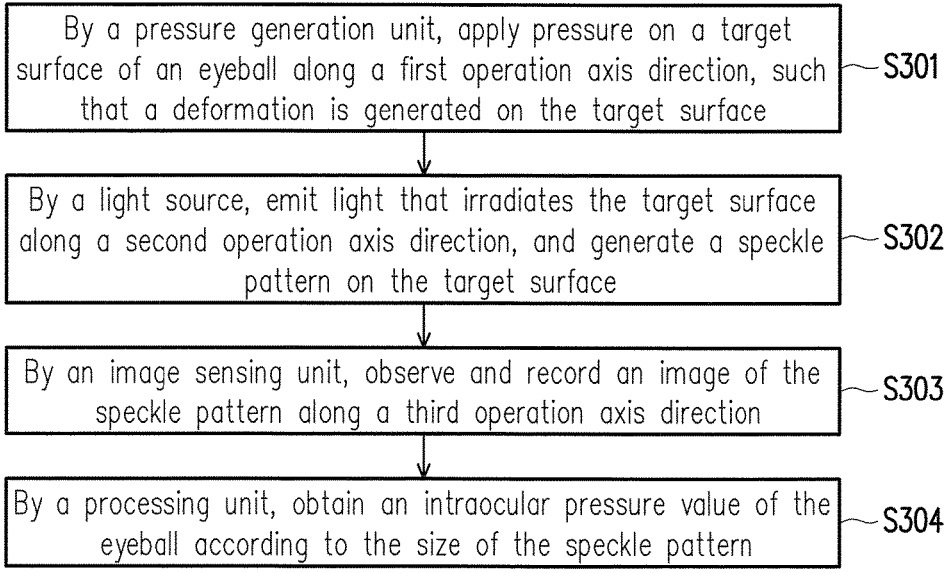
FIG. 10 is a schematic flow chart diagram of an intraocular pressure detecting method according to an exemplary embodiment of the disclosure.

FIG. 10 is a schematic flow chart diagram of an intraocular pressure detecting method according to an exemplary embodiment of the disclosure. Referring to FIGS. 1 and 10, the detecting method in the present exemplary embodiment includes the following steps. Pressure is applied by the pressure generation unit 110 to the target surface 52 of the eyeball 50 along the first operation axis direction A1, such that a deformation is generated on the target surface 52 of the eyeball 50 (step S301). Next, light is emitted by the light source 120 and irradiates the target surface 52 of the eyeball 50 along the second operation axis direction A2, and the speckle pattern 60 is generated on the target surface 52 (step S302). Then, the contour of the speckle pattern 60 is observed and recorded by the image sensing unit 130 along the third operation axis direction A3 (step S303). Next, an intraocular pressure value of the eyeball 50 is obtained by the processing unit 150 according to the size of the speckle pattern 60 (step S304).

In the step of obtaining the intraocular pressure value of the eyeball 50 by the processing unit 150, the pressure generation unit 110 applies pressure to the target surface 52 of the eyeball 50 by, e.g., air-puff jetting, such that a normal external loading force is generated on the target surface 52. In addition, before measurement, the processing unit 150 is subjected to a corresponding correction according to at least two standard intraocular pressure values and the corresponding sizes of the speckle pattern 60 obtained using the medical tonometer instrument such as a Goldmann applanation tonometer, a non-contact tonometer or any other tonometer accredited by medical institutes. The processing unit 150 has a built-in relation function between the speckle pattern 60 and intraocular pressure value, and establishes a lookup table, so as to instantly convert the measured size of the speckle pattern 60 into the corresponding actual intraocular pressure value.

In the step of receiving the image of the speckle pattern 60 and identifying and analyzing the size of the speckle pattern 60 by the processing unit 150 so as to obtain the intraocular pressure value, the image sensing unit 130 captures an image of the speckle pattern 60 to obtain a dynamic images or a static image of the speckle pattern 60. The dynamic image captured by the image sensing unit 130 is also converted by the processing unit 150 into static images at various time points. The processing unit 150 receives the image captured by the image sensing unit 130, and selects from all the images an image of the speckle pattern 60 for subsequent identification and analysis, wherein the selecting is carried out by, e.g., selecting an image of the speckle pattern 60 having a larger feature size. Then, the processing unit 150 carries out the subsequent identification and analysis, and calculation and conversion for the intraocular pressure value according to the selected image of the speckle pattern 60.

In the present exemplary embodiment, the patient presets at least two or a set of thresholds in the application software of the processing unit 150 in accordance with the doctor's instructions, so as to define a normal range, a warning range and a dangerous range of the intraocular pressure value. The processing unit 150 directly compares the obtained size of the speckle pattern 60 and the corresponding intraocular pressure value with the above thresholds, thereby determining whether the patient's intraocular pressure is within the normal range.

When the intraocular pressure value is outside the thresholds for the normal range, the processing unit 150 issues a notification through the application software to alert the patient to take medication or go to the doctor as soon as possible. In addition, the application software of the processing unit 150 also assists the patient with daily intraocular pressure management, associates the patient's intraocular pressure information with a medical record database of the hospital via a cloud platform, and further transmits a message indicative of abnormal intraocular pressure to a relevant medical unit in real time for performing monitoring. For example, the processing unit 150 transmits the message indicative of abnormal intraocular pressure to an ophthalmologist whom the patient consults, and the patient may be notified to return to the doctor if necessary.

In summary, in the intraocular pressure detecting device and method according to the exemplary embodiments of the disclosure, pressure is applied by the pressure generation unit to the target surface of the eyeball, such that a deformation is generated on the target surface. The light source irradiates the deformed target surface of the eyeball, and generates the speckle pattern on the target surface. Next, the processing unit subjects the image of the speckle pattern captured by the image sensing unit to selection and identification, so as to obtain the intraocular pressure value of the eyeball. In the way of detecting intraocular pressure provided by the exemplary embodiments of the disclosure, there is no need to measure deformation of an eyeball cornea in the operation axis direction in a complex or invasive manner, and the intraocular pressure value of the eyeball can be directly inferred according to the size of the speckle pattern on the cornea, i.e., by observing transverse deformation of the cornea. Moreover, by determining whether the intraocular pressure at that moment exceeds a predetermined threshold, it is possible to alert the patient in real time to take medication or go to the doctor. Therefore, the disclosure provides a simple intraocular pressure measurement means for use at home to thereby enable the patient to easily perform self-detection outside the hospital or clinic, and further provides a tonometer that is easy and safe to use and that is capable of 24-hour intraocular pressure monitoring.

In addition, according to the exemplary embodiments of the disclosure, variation in the speckle pattern in the eye on the corneal surface is observed by a holographic image, so that the intraocular pressure is determined in real time. Moreover, the architecture is simple, and thus precision optical and force sensing devices essential to a conventional non-contact tonometer can be replaced. Also, the exemplary embodiments of the disclosure have a microminiaturized body and a price advantage. Due to differences (such as corneal thickness, curvature, diameter and material properties) between entities contained in the measurement results of images of the speckle pattern, a personalized intraocular pressure characteristic curve is established accordingly, and a personal intraocular pressure quick lookup table is configured and provided based on the curve and the thresholds. Since target and baseline IOPs and suitable treatment policies (such as prescriptions, frequency of administration, timing of administration, and dosage, etc.) can be personalized for an individual patient according to fluctuation information of the patient's intraocular pressure obtained by measurement at home, new business models and new values could be generated for the industry of clinical diagnosis of glaucoma-related diseases.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. An intraocular pressure detecting device, comprising:
  a pressure generator, configured to apply pressure to a target surface of an eyeball along a first operation axis direction, such that a deformation is generated on the target surface;
  a light emitting device, configured to emit a light that irradiates the target surface along a second operation axis direction, so as to generate a speckle pattern on the target surface;
  a camera, configured to capture and record an image variation of the speckle pattern along a third operation axis direction; and
  a processor, signally connected with the camera to receive an image of the speckle pattern, the processor identifying and analyzing a feature size of the image of the speckle pattern, so as to obtain an intraocular pressure value of the eyeball,
  wherein when the processor receives the image of the speckle pattern, and identifies and analyzes the feature size of the speckle pattern so as to obtain the intraocular pressure value of the eyeball, the camera captures the image of the speckle pattern, so as to obtain at least one dynamic image or a plurality of static images of the speckle pattern, the processor receives the dynamic image or the static images captured by the camera, and selects therefrom the image of the speckle pattern for identification and the processor identifies and analyzes the feature size of the image of the speckle pattern.

2. The intraocular pressure detecting device of claim 1, wherein the target surface is located on a cornea of the eyeball.

3. The intraocular pressure detecting device of claim 2, wherein the cornea is a natural human cornea or an artificial cornea.

4. The intraocular pressure detecting device of claim 1, wherein a size of the speckle pattern and the intraocular pressure value have a negative correlation with each other.

5. The intraocular pressure detecting device of claim 1, wherein the processor is set to have at least one threshold, and when the intraocular pressure value is larger or smaller than the threshold, the processor issues a notification.

6. The intraocular pressure detecting device of claim 5, wherein the processor comprises a software, and the software executes a setting procedure of the at least one threshold and a correspondence procedure of at least two standard correction intraocular pressure values and diaphragm values.

7. The intraocular pressure detecting device of claim 1, wherein the pressure generator applies pressure to the target surface in a non-contact manner, and the non-contact manner comprises pressure application by air, gases, sound waves or electromagnetic waves.

8. The intraocular pressure detecting device of claim 1, wherein the pressure generator comprises an external gas source, a pressure regulating valve, a gas filter, a gas valve and a gas nozzle, wherein the gas nozzle is connected to the gas valve, and the gas valve is disposed between the pressure regulating valve and the gas nozzle.

9. The intraocular pressure detecting device of claim 1, wherein the light emitting device comprises visible light and invisible light, and the invisible light has a wavelength ranging from 800 to 1064 nm.

10. The intraocular pressure detecting device of claim 1, wherein the camera comprises a photosensitive device, a lens set, an image storage device and a control circuit.

11. The intraocular pressure detecting device of claim 1, wherein an angle between the first operation axis direction and the second operation axis direction falls between 0 and 90 degrees, an angle between the second operation axis direction and the third operation axis direction falls between 0 and 180 degrees, and an angle between the first operation axis direction and the third operation axis direction falls between 0 and 90 degrees.

12. An intraocular pressure detecting method, comprising:
  by a pressure generator, applying pressure to a target surface of an eyeball along a first operation axis direction, such that a deformation is generated on the target surface;
  by a light emitting device, emitting a light that irradiates the target surface along a second operation axis direction, and generating a speckle pattern on the target surface;
  by a camera, capturing and recording an image variation of the speckle pattern along a third operation axis direction; and
  by a processor, receiving an image of the speckle pattern, and identifying and analyzing a feature size of the image of the speckle pattern, so as to obtain an intraocular pressure value of the eyeball,
  wherein the step of receiving the image of the speckle pattern, and identifying and analyzing the feature size of the speckle pattern by the processor so as to obtain the intraocular pressure value of the eyeball comprises:

by the camera, capturing the image of the speckle pattern, so as to obtain at least one dynamic image or a plurality of static images of the speckle pattern;

by the processor, receiving the dynamic image or the static images captured by the camera, and selecting therefrom the image of the speckle pattern for identification; and by the processor, identifying and analyzing the feature size of the image of the speckle pattern.

13. The intraocular pressure detecting method of claim 12, further comprising setting at least one threshold at the processor and comparing the intraocular pressure value with the threshold by the processor, wherein when the intraocular pressure value is larger than or smaller than the threshold, the processor issues a notification.

14. The intraocular pressure detecting method of claim 12, further comprising, before identifying and analyzing the feature size of the image of the speckle pattern by the processor, obtaining at least two intraocular pressure detection standard values and corresponding feature sizes of the speckle patterns using a medical tonometer.

15. The intraocular pressure detecting method of claim 14, further comprising obtaining a corresponding function according to the at least two intraocular pressure detection standard values and the corresponding feature sizes of the speckle patterns, and using the corresponding function as a basis of a correspondence between the feature size of the speckle pattern and the intraocular pressure value.

16. The intraocular pressure detecting method of claim 15, wherein the corresponding function is a linearly monotonic function or a nonlinearly monotonic function.

17. The intraocular pressure detecting method of claim 12, wherein the step of applying pressure to the target surface by the pressure generator further comprises performing pulse jetting to the target surface along the first operation axis direction.

* * * * *